(12) United States Patent
Prior et al.

(10) Patent No.: US 6,391,196 B1
(45) Date of Patent: May 21, 2002

(54) CHROMATOGRAPHY APPARATUS

(75) Inventors: Adalbert Prior, Gotzis; Jurgen Wolfgang, Bregenz, both of (AT)

(73) Assignee: Prior Separation Technology GmbH, Gotzis (AT)

( * ) Notice: Subject to any disclaimer, the term of this patent is extended or adjusted under 35 U.S.C. 154(b) by 0 days.

(21) Appl. No.: 09/486,321

(22) PCT Filed: Aug. 28, 1998

(86) PCT No.: PCT/AT98/02205

§ 371 Date: Mar. 21, 2000

§ 102(e) Date: Mar. 21, 2000

(87) PCT Pub. No.: WO99/12625

PCT Pub. Date: Mar. 18, 1999

(30) Foreign Application Priority Data

Sep. 8, 1997 (AT) .......................................... 554/97 U

(51) Int. Cl.⁷ .............................................. B01D 15/08
(52) U.S. Cl. ................... 210/198.2; 210/656; 210/657; 210/659
(58) Field of Search ................. 210/656, 657, 210/198.2, 635, 659

(56) References Cited

U.S. PATENT DOCUMENTS

| | | | |
|---|---|---|---|
| 2,708,519 A | * 5/1955 | Novak | 210/657 |
| 3,077,103 A | 2/1963 | Heaton | 73/23.1 |
| 3,257,781 A | 6/1966 | Debbrecht et al. | 55/197 |
| 3,617,557 A | 11/1971 | Giltrow | 210/198.3 |
| 3,666,105 A | * 5/1972 | Fox | 210/198.2 |
| 3,732,982 A | * 5/1973 | Dunnill | 210/657 |
| 4,107,041 A | * 8/1978 | Karlson | 210/198.2 |
| 4,642,169 A | * 2/1987 | Yoshisato | 204/180.1 |
| 4,808,317 A | 2/1989 | Berry et al. | 210/660 |
| 5,024,749 A | * 6/1991 | Snyder | 210/198.2 |
| 5,045,209 A | * 9/1991 | Snyder | 210/656 |
| 5,110,566 A | * 5/1992 | Snyder | 210/656 |
| 5,124,023 A | * 6/1992 | Bosserman | 210/657 |
| 5,133,869 A | * 7/1992 | Taniguchi | 210/657 |
| 5,149,436 A | * 9/1992 | Taniguchi | 210/657 |
| 5,437,795 A | * 8/1995 | Snyder | 210/657 |
| 5,725,762 A | * 3/1998 | Beal | 210/181 |

FOREIGN PATENT DOCUMENTS

| | | | |
|---|---|---|---|
| DE | 24 40 848 | 3/1976 | 210/198.2 |
| EP | 0 371 648 A1 | 6/1990 | 210/198.2 |
| EP | 0 452 826 A2 | 10/1991 | 210/198.2 |

* cited by examiner

Primary Examiner—Ernest G. Therkorn
(74) Attorney, Agent, or Firm—Oliff & Berridge, PLC

(57) ABSTRACT

Disclosed is an assembly for continuous annular chromatography provided with a relative movement between one partial bed in the form of a cylinder jacket, at least one feeding position for liquid feeding material and at least one collection position for every emerging fraction of the feeding material out of the partial bed.

10 Claims, 1 Drawing Sheet

CHROMATOGRAPHY APPARATUS

REFERENCE TO RELATED APPLICATIONS

This application is a 371 of PCT/AT98/00205 Aug. 28/1998.

The invention relates to an apparatus for continuous annular chromatography, in which a relative movement between a particle bed in the form of a cylindrical jacket and at least one feed point for liquid feed material and at least one collection point for each feed material fraction emerging from the particle bed is provided by rotating the particle bed.

In column chromatography, a vertical cylinder is filled with particulate material and loaded at the top with a mixture of components which is to be separated. Elution is then effected continuously from the top with a solvent, the components, owing to their different affinities to the particle material, being separated in proportion to the flow rate of the solvent (eluent) and leaving the column in succession.

A distinction is made between the use of a single solvent (isocratic procedure) and the use of a plurality of different solvents (step or gradient procedure). In the step procedure, the solvent is changed without a transition; in the gradient procedure, the proportion of individual solvents in a solvent mixture is changed as a function of time.

In this elution chromatography, the components are simply washed through the column; if, on the other hand, a so-called displacer is used in the eluent, i.e. a component which has a higher affinity to the particle material than all previously added components and therefore displaces said components, the term used is displacement chromatography, in which fractions concentrated in comparison with elution chromatography are obtained, but not all of the individual components is obtainable in pure form (mixtures are always obtained).

Annular chromatography, in which a relative movement between a particle bed in the form of a vertical cylindrical jacket and at least one feed point arranged at the top of said jacket and intended for liquid feed material is provided and the individual components pass through the particle material along spiral paths and emerge simultaneously along the lower circumference of the cylindrical jacket in different circumferential regions, was developed to permit continuous chromatography. It can be used, for example, as HPLC, elution or displacement chromatography and is operated, in particular, isocratically. Continuous annular chromatography is abbreviated internationally to CAC.

Both apparatuses in which the particle bed is stationary and those in which the particle bed rotates relative to feed point(s) and collection points are known for CAC. EP-A 371 648 of Union Oil of California may be mentioned as an example of a publication which describes in detail the apparatuses of the second type, which are to be further developed by the present invention, and gives an overview of a very wide range of chromatographic methods.

U.S. Pat. No. 3,077,103 proposes a closed CAC apparatus in which the annular cylindrical chromatography jacket is mounted between two round end pieces. Two concentric side walls which form a furrow into which the chromatography jacket is rotatably inserted each project from the surfaces of the two end pieces. O-rings for guiding the chromatography jacket are provided between the outer walls of the cylindrical jacket and the inner surfaces of the side walls. To prevent bonding of the cylindrical jacket base at the bottom of the furrow, the jacket base is guided a distance away from the bottom of the furrow.

The object of the invention is to propose a simple measure which enables CAC apparatuses to be made insensitive to contamination by the environment, in particular to permit sterile operation.

Accordingly, in the apparatus according to the invention for continuous annular chromatography, in which a relative movement between a particle bed in the form of a cylindrical jacket and at least one collection point for each feed material fraction emerging from the particle bed is provided by rotating the particle bed, the baseplate of the annular cylindrical chromatography jacket rests on the collecting ring for the fractions emerging from the feed material and slides while providing a seal.

The otherwise usual discharge nozzles for the fractions emerging from the CAC column are in the form of channels in the liquid exit zone of the particle bed jacket—in other words, liquid channels running at least essentially parallel to the axial direction of the particle bed in the direction of the collecting ring and arranged equal distances apart are provided in the liquid exit zone of the particle bed jacket below the particle bed.

Furthermore, it is advantageous that a liquid-permeable strip for retaining bed material, in particular a strip of porous plastic, is provided between particle bed and liquid channels.

A further design according to the invention is that a wedge space adjoins each of the liquid channels in the direction of the particle bed.

DESCRIPTION OF THE PREFERRED EMBODIMENTS

Figure 1:
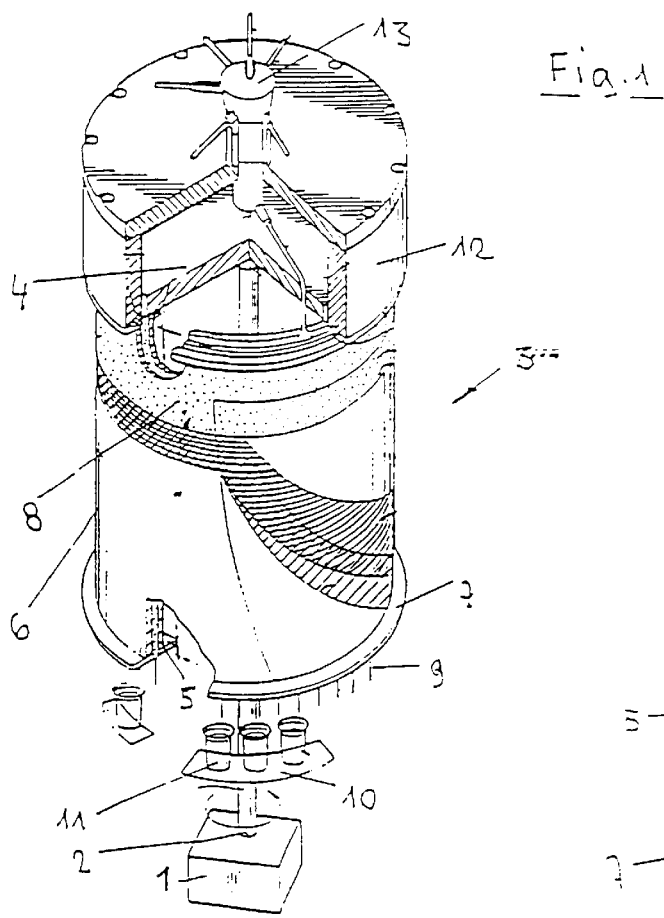
FIG. 1 shows a prior art CAC.
Figure 2:
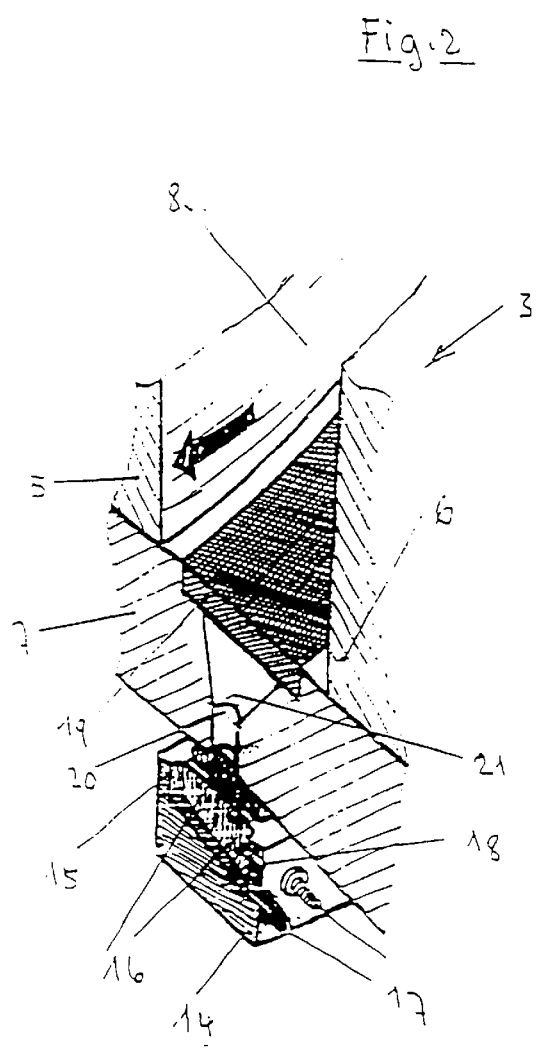
FIG. 2 shows a section of a design according to the present invention.
Figure 3:
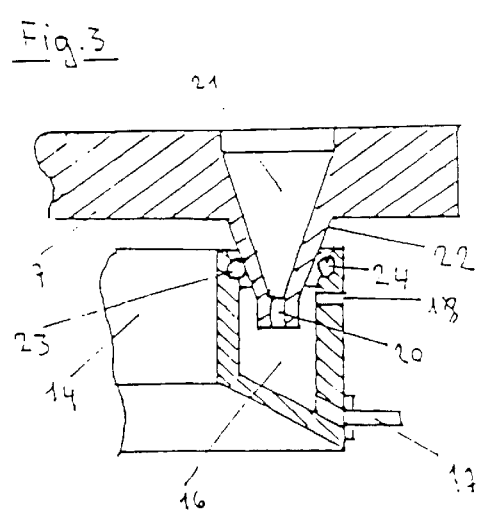
FIG. 3 shows part of a second embodiment according to the present invention.

The invention is explained in more detail below on the basis of an embodiment and with reference to the drawing, in which FIGS. 1 and 2 are each partially cut away oblique views, wherein FIG. 1 shows the prior art according to EP-A 371 648 for explaining the function of CAC with a rotating particle bed and FIG. 2 and 3 show examples according to the invention, identical components bearing the same reference symbols.

From FIG. 1, it is evident that a rotary element 3 which is cylindrical over an axle 2 driven in the direction indicated by the arrow (counterclockwise) rests on a support 1, said rotary element 3 possessing an inner wall S [sic] having a conical roof 4 and an outer wall 6 which is open at the top and rests on a baseplate 7. Between inner wall s [sic] and outer wall 6 is a cylindrical bed 8 comprising particulate material, for example a suitable ion-exchange resin. The baseplate 7 has, in the region of the bed, holes which have discharge nozzles 9 for liquid which passes downward through the bed and positioned on a nonrotatable annular platform 10.

Located above the rotary element 3 is a material feed cap 12 which is likewise nonrotatable and has a central feed 13 via which, on the one hand, solvent as a material transport vehicle is introduced centrally onto the conical roof 4 of the inner wall 5 and, on the other hand, liquid mixture to be separated is introduced at certain points peripherally at the top of the bed, distributed over the circumference of the bed, and treatment agents, such as, for example, displacement substances, are introduced at other points. The individual fractions pass through the bed along curved paths before they emerge from the bed at the bottom.

FIG. 2 shows a section of a design according to the invention, which shows the lower end of the rotary element 3 and in which the reference symbols used are the same as those in FIG. 1. The direction of rotation indicated by the arrow is opposite of that in FIG. 1, but this makes essentially no difference. The baseplate 7 slides on a collecting ring 14 which corresponds to the annular platform 10 in FIG. 1 and has chambers 16 which are separated along the circumference of said collecting ring 14 by radial walls 15 and correspond to the collecting containers 11 in FIG. 1, have a base inclined downward toward the outer circumference of the collecting ring 14 and open into discharge nozzles 17. 18 denotes a pressure equilibration orifice which is covered by a sterile filter membrane during sterile operation:

The bed 8 is merely indicated—the baseplate 7 has a central strip for retaining bed material, in the form of a filter web 19, through which fractionated liquid emerging from the apparatus flows away via liquid channels 20 into the chamber 16. FIG. 2 shows that the width of the strip for retaining bed material is in each case a multiple of the diameter of the serve for uniform distribution of the liquid emerging from the bed, regardless of whether, according to a further design according to the invention and applicable in all CAC apparatuses, the volume of the bed material is varied using inner walls 5 of different diameters. The strip for retaining bed material consists of a material adapted to the feed material, for example metal in the case of an organic solvent, porous plastic at acidic pH and porous ceramic in the alkaline range.

Preferably, the upper side of the collecting ring 14 and/or the underside of the baseplate 7 have a friction-reducing coating in the contact region.

FIG. 3 shows part of the second embodiment, in which only the rotating baseplate 7 need be surface-treated, but not the stationary collecting ring 14. The baseplate 7 has, on its take-off side, an all-round conical rib 22 whose conical surfaces are faced, and the collecting ring 14 has all-round ring seals for two O-rings 23, 24, the O-rings being subject to virtually no wear since the baseplate 7 turns only very slowly.

The collecting ring 14 is merely placed against the baseplate 7 from below. Various types of ring seals are commercially available, including those having a V-cross-section in which one limb is flatly abutting and the other is pressed against the corresponding component. All such ring seals may be used here, including of course more complicated ring seals having two components rotatable against one another.

What is claimed is:

1. An apparatus for continuous annular chromatography of liquid feed material, comprising:
   at least one feed point for liquid feed material;
   an upright cylindrical jacket rotatable about its axis and filled with a particle bed;
   a base plate which is connected to the cylindrical jacket; and
   a collecting ring adjacent the base plate, wherein the cylindrical jacket comprising said particle bed rotates relative to said at least one feed point and to said collecting ring and the base plate rests on the collecting ring and slides while providing a seal, wherein the base plate further contains liquid channels widening towards the particle bed and connecting the particle bed with the collecting ring, and wherein the collecting ring comprises chambers separated by radial walls, each chamber comprising a means for pressure equilibration.

2. The apparatus as claimed in claim 1, wherein either or both of an upper side of the collecting ring and an underside of the base plate have a friction-reducing coating in the contact region.

3. The apparatus according to claim 1, wherein each liquid channel widens in the form of a wedge space towards the particle bed.

4. The apparatus according to claim 1, wherein said means for pressure equilibration is an orifice.

5. The apparatus according to claim 4, wherein said orifice is covered by a filter membrane.

6. The apparatus according to claim 1, wherein a liquid-permeable strip for retaining bed material is provided between particle bed and liquid channels.

7. The apparatus according to claim 1, wherein a liquid-permeable strip for retaining bed material is provided between particle bed and liquid channels.

8. An apparatus for continuous annular chromatography of liquid feed material, comprising:
   at least one feed point for liquid feed material;
   an upright cylindrical jacket rotatable about its axis and filled with a particle bed;
   a base plate which is connected to the cylindrical jacket; and
   a collecting ring adjacent the base plate, wherein the cylindrical jacket comprising said particle bed rotates relative to said at least one feed point and to said collecting ring and the base plate rests on the collecting ring and slides while providing a seal, wherein the base plate further contains liquid channels widening towards the particle bed and connecting the particle bed with the collecting ring, and wherein the collecting ring comprises chambers separated by radial walls that are thinner than a cross-sectional diameter of the channels.

9. The apparatus according to claim 8, wherein each chamber comprises a means for pressure equilibration.

10. The apparatus according to claim 9, wherein said means for pressure equilibration is an orifice.

* * * * *